(12) United States Patent
Trapeznikov

(10) Patent No.: US 12,016,789 B2
(45) Date of Patent: Jun. 25, 2024

(54) DEVICE AND METHOD FOR SECURELY POSITIONING A CORONARY STENT INSIDE CORONARY ARTERIES

(71) Applicant: SEVEN SONS LTD. R.N. 515985570 (THE "COMPANY"), Tel Aviv (IL)

(72) Inventor: Vladimir Borisovich Trapeznikov, Moscow (RU)

(73) Assignee: Seven Sons Ltd., Tel Aviv (IL)

( * ) Notice: Subject to any disclaimer, the term of this patent is extended or adjusted under 35 U.S.C. 154(b) by 1140 days.

(21) Appl. No.: 16/604,717

(22) PCT Filed: Jul. 27, 2017

(86) PCT No.: PCT/RU2017/000555
§ 371 (c)(1),
(2) Date: Oct. 11, 2019

(87) PCT Pub. No.: WO2018/190745
PCT Pub. Date: Oct. 18, 2018

(65) Prior Publication Data
US 2020/0222217 A1    Jul. 16, 2020

(30) Foreign Application Priority Data

Apr. 12, 2017    (RU) .......................... RU2017112500

(51) Int. Cl.
*A61F 2/95*     (2013.01)
*A61M 25/01*    (2006.01)
*A61M 25/09*    (2006.01)

(52) U.S. Cl.
CPC ........... *A61F 2/95* (2013.01); *A61M 25/0113* (2013.01); *A61F 2/9517* (2020.05); *A61M 2025/09116* (2013.01)

(58) Field of Classification Search
CPC ... A61B 17/95; A61B 17/9517; A61B 17/962; A61B 17/966; A61B 17/2909;
(Continued)

(56) References Cited

U.S. PATENT DOCUMENTS 5,114,403 A * 5/1992 Clarke ................. A61M 25/01
  604/95.04
5,137,288 A * 8/1992 Starkey ................ A61M 25/09
  279/42

(Continued)

FOREIGN PATENT DOCUMENTS

RU    2 598 798 C1    9/2015

OTHER PUBLICATIONS

International Search Report in International Application No. PCT/RU2017/000555.
(Continued)

*Primary Examiner* — Darwin P Erezo
*Assistant Examiner* — Christian D Knauss
(74) *Attorney, Agent, or Firm* — Ladas & Parry LLP

(57) ABSTRACT

A device for positioning a coronary stent within coronary arteries is described. The device has a housing having a cylindrical front part and an internally-threaded cylindrical rear part connected to each other by a slot allowing the cylindrical rear part to rotate around an axis. The cylindrical front part of the housing is provided with recesses for fixing a coronary guide. A runner is provided with projections for engaging an internal thread of the cylindrical rear part of the housing. The device includes a structure for clamping disposed in a threaded runner cap. The runner is disposed inside a retainer with ears projecting into side holes on both sides of the housing. Clamping is operable by rotation of the rear part of the device housing. A method for positioning a coronary stent within coronary arteries is also described.

3 Claims, 11 Drawing Sheets

Figure 1:
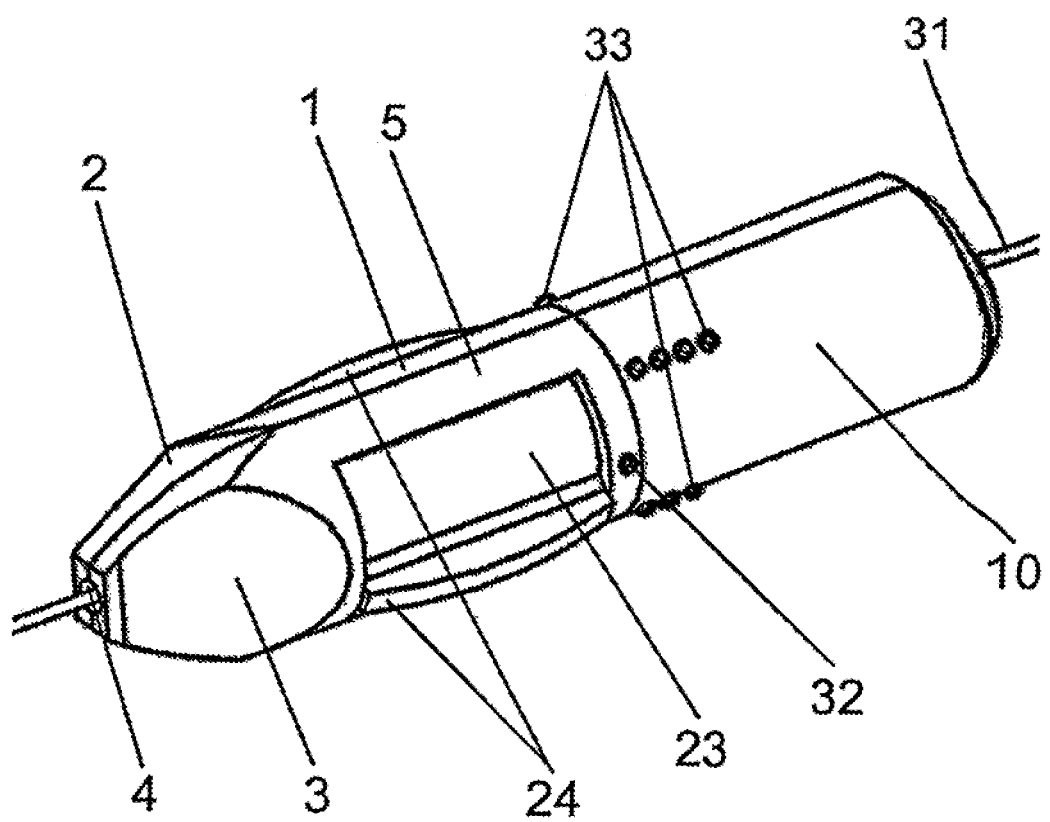

(58) Field of Classification Search
CPC .......... A61B 2017/2912; A61M 25/01; A61M 25/0113; A61M 25/0136; A61M 25/09041; A61M 2025/09116; A61F 2/95; A61F 2/9517; A61F 2/962; A61F 2/966
See application file for complete search history.

(56) References Cited

U.S. PATENT DOCUMENTS

| | | | | |
|---|---|---|---|---|
| 5,161,534 | A * | 11/1992 | Berthiaume | .......... A61M 25/01 226/127 |
| 6,203,550 | B1 * | 3/2001 | Olson | ..................... A61F 2/954 606/108 |
| 6,293,964 | B1 | 9/2001 | Yadav | |
| 6,533,772 | B1 * | 3/2003 | Sherts | ............... A61M 25/0136 279/42 |
| 2012/0221091 | A1 | 8/2012 | Hartly et al. | |
| 2013/0274870 | A1 | 10/2013 | Lombardi et al. | |
| 2015/0045871 | A1 * | 2/2015 | Beckham | ................ A61F 2/966 623/1.11 |

OTHER PUBLICATIONS

Written Opinion of the International Search Authority in International Application No. PCT/RU2017/000535.

* cited by examiner

DEVICE AND METHOD FOR SECURELY POSITIONING A CORONARY STENT INSIDE CORONARY ARTERIES

RELATED APPLICATION

This application is an application under 35 U.S.C. 371 of International Application No. PCT/RU2017/000555 filed on 27 Jul. 2017, which claims priority from Russian Application No. 2017112500 filed 12 Apr. 2017, the disclosures of which are incorporated in their entirety by reference herein.

The present invention is suitable for use in medicine for maximally accurate, fast and safe positioning a coronary stent in case of uncomplicated and complicated coronary bed lesions, specifically, within a coronary artery in case of endovascular coronary stenting to restore the lumen of artery portions narrowed due to a lesion.

The device according to the invention is intended for use in case of ostial lesions of coronary arteries, bifurcation lesions of coronary arteries, including lesions of the left coronary artery trunk and the right coronary artery ostium, and also in case of "stent-in-stent" coronary stenting to reduce the "overlap" zone.

The use of this device allows the radiation exposure of patients and medical personnel as well as the exposure of patients to radio-opaque contrast agents to be significantly reduced.

The device may be easily used by young professionals at a time of their professional development in the field of interventional cardiology.

In addition, the claimed device may be also used for stenting renal, visceral arteries in a similar way.

A number of devices for coronary stenting are available at the medical equipment market.

In particular, U.S. Pat. No. 6,293,964 discloses OSTIAL PRO available from Merit Medica (USA). The device according to this patent comprises a cone made up of four tongues insertable into a guiding catheter together with a coronary stent. The guiding catheter is selectively positioned within the coronary ostium. The coronary stent is guided along the catheter to a location more distal that the coronary ostium and the guiding catheter is then withdrawn from the coronary ostium and the device is deployed. As the device leaves the guiding catheter, its tongues unfold and abut against the aortal wall so that the guiding catheter tip cannot be selectively positioned within the coronary ostium as required for ostial stenting of the left coronary artery trunk and the right coronary artery trunk. The entire subsequent positioning the coronary stent within an affected area is performed manually.

A disadvantage of the known device is its limited applicability, in particular only in cases of ostial lesions of the left coronary artery trunk and the right coronary artery trunk, as well as the manual positioning of the coronary stent.

Also known is "Device for a safe positioning a coronary stent within coronary arteries" according to RU Patent No. 2598798 owned by Seven Sons OJSC.

The claimed device differs primarily in:
  faster and more accurate positioning a coronary stent within a coronary artery,
  mechanical positioning rather than manual positioning the stent,
  reduced radiation exposure of patients and medical personnel due to reduced time of the coronary stent positioning,
  applicability of the device in case of lesions within any segment of the coronary bed,
  reduced exposure of patients to radio-opaque contrast agents due to reduced time of the coronary stent positioning,
  single application,
  the device is conveniently configured as an extension of the surgeon's arm,
  minimal weight and dimensional parameters,
  ease of use,
  cost-effective production.

The claimed device comprises a housing having a runner disposed therein, said runner having a hole for receiving a delivery system, projections for engaging an internal thread in a cylindrical rear part of the housing and projections for moving along guides inside the housing on the one side, and a metal collet accommodated therein with a hole for receiving a delivery system and hooks, said collet disposed in a cap with a hole for receiving a delivery system and provided with a thread to be screwed on the runner on the other side.

The housing formed of a truncated cylindrical front part and a cylindrical rear part connected to each other by a circumferentially extending slot is made of plastic and is provided with recesses for operator's fingers on both sides of the truncated cylindrical front part of the housing, wherein the right and left halves of the body are manufactured separately and connected to each other once the mechanism has been assembled with the aid of projections and holes arranged on the edges of the inner part of the housing. On the front part of the housing along the slot connecting the front part to the rear part of the housing and also on the rear part of the housing, special marks are arranged providing additional visual information to the operator as to the rotation angle of the rear part of the housing as the runner moves.

The cylindrical front part of the housing is provided with a retainer having ears projecting into the side holes on both sides of the housing inside which a cap is arranged threadedly connected to the runner accommodating a collet with hooks.

In the truncated front part of the housing adapted for being held with the operator's left thumb and left forefinger, recesses are formed allowing the operator to fix the device in position, wherein the left thumb recess also serves as a pad for fixing a coronary guide. Through-holes for insertion of the coronary stent delivery system into the housing are formed in the front and rear parts of the housing.

A slot is formed in the housing between its cylindrical front part and cylindrical rear part, connecting both parts such that the cylindrical rear part is rotatable around its axis.

Accommodated in side cutouts on the front part of the housing are the ears of the retainer arranged inside the cylindrical front part of the housing, said ears allowing the retainer to be rotatable relative to the housing in the slots of which projections are arranged on the runner cup accommodating hooks of the runner collet, said hooks, once engaged, causing the cap to rotate in one or another direction, as the cap becomes either screwed on or off the runner and thereby either collapsing or expanding the collet hooks and accordingly clamping or releasing the coronary stent delivery system. At the same time, the cap moves horizontally along the same slots together with the runner as the cylindrical rear part of the housing rotates at the point of the connection slot.

The retainer is formed such that as it is caused to rotate with the aid of ears provided in the side cutouts in the cylindrical front part of the housing, the cap rotates to become screwed on or off with the collet inside, wherein the collet hooks open and close depending on the cap position, and as the cylindrical rear part of the housing rotates around its axis, the runner moves horizontally along the guides of the front part of the housing once its projections have engaged the internal thread in the cylindrical rear part of the housing. The coronary stent delivery system arranged in the runner moves simultaneously with the runner while the collet hooks are clamped.

In order to return the retention mechanism to its initial position, the retainer and the cylindrical rear part of the housing are caused to operate in reverse direction.

Such design makes it possible to rigidly fix the coronary stent delivery system as the stent moves both forwards and backwards while allowing the same to rotate simultaneously around its axis because while the collet hooks are clamped, the collet is freely rotatable around its axis.

Thus, as the cap is screwed off the runner body due to rotation of the retainer ears, the collet hooks open so that the coronary stent delivery system is in a free state enabling its free axial displacement and, once the cap is screwed on, the collet hooks close to fix the delivery system.

When the device is prepared for use, a coronary stent carried by a delivery system is first progressively inserted inside the device while the collet hooks are open and the coronary stent delivery system is placed via through-holes provided in the housing. The operator manually advances the coronary stent carried by the delivery system placed within the device to the affected area of a coronary artery. Then, the operator brings the device to a necessary distance for fixing the same with his/her left arm, fixes the deliver system with the aid of collet hooks by means of rotating the retainer with his/her right hand and further rotates the cylindrical rear part of the housing to convert rotary motion of the housing into translational motion of the runner, and advances the delivery system to a necessary distance for positioning the coronary stent inside the vessel. When advancing the rear part of the housing, the operator may also return the mechanism retaining the coronary stent delivery system into its initial position by means of rotating the cylindrical rear part of the housing in the necessary direction so that further positioning of the coronary stent either forwards or backwards may be continued.

Exemplary Embodiment 2

The device comprises a housing having a runner disposed therein, said runner having a hole for receiving a delivery system, projections for engaging an internal thread in a cylindrical rear part of the housing, projections for moving along guides inside the housing on the one side, and a plastic clamp provided with a hole for receiving a delivery system, formed integrally with the runner, placed in a cap with a hole for receiving the delivery system and provided with a thread to be screwed on the runner on the other side.

The housing formed of a truncated cylindrical front part and a cylindrical rear part connected to each other by a circumferentially extending slot is made of plastic and is provided with recesses for operator's finger on both sides of the truncated cylindrical front part of the housing, wherein the right and left halves of the body are manufactured separately and connected to each other once the mechanism has been assembled with the aid of projections and holes arranged on the edges of the inner part of the housing.

The cylindrical front part of the housing is provided with a retainer having ears projecting into the side holes on both sides of the housing inside which a cap is arranged threadedly connected to the runner accommodating a plastic clamp.

In the truncated front part of the housing adapted for being held with the operator's left thumb and left forefinger, recesses are formed allowing the operator to fix the device in position, wherein the left thumb recess also serves as a pad for fixing a coronary guide. Through-holes for insertion of the coronary stent delivery system into the housing are formed in the front and rear parts of the housing.

A circumferential slot is formed in the housing between its cylindrical front part and cylindrical rear part, connecting both parts such that the cylindrical rear part is rotatable around its axis.

Accommodated in side cutouts on the front part of the housing are the ears of the retainer arranged inside the housing, said ears allowing the retainer to be rotatable relative to the housing in the slots of which projections are arranged on the runner cup accommodating a plastic clamp formed integrally with the runner, said clamp, once engaged, causing the cap to rotate in one or another direction as the cap either screws on or off the runner and thereby compressing or expanding the plastic clamp flaps respectively clamping or releasing the coronary stent delivery system. At the same time, the cap moves horizontally along the same slots together with the runner as the cylindrical rear part of the housing rotates at the point of the connection slot.

The retainer is formed such that as it is caused to rotate with the aid of ears provided in the side cutouts in the cylindrical front part of the housing, the cap rotates to become screwed on or off with the collet inside, wherein the collet hooks open and close depending on the cap position and, as the cylindrical rear part of the housing rotates around its axis, the runner moves horizontally along the guides of the front part of the housing once its projections have engaged the internal thread in the cylindrical rear part of the housing. The coronary stent delivery system arranged in the runner moves simultaneously with the runner while the collet retainers are clamped.

In order to return the retention mechanism to its initial position, the retainer and the cylindrical rear part of the housing are caused to operate in reverse direction.

Such design makes it possible to rigidly fix the coronary stent delivery system as the stent moves both forwards and backwards.

Thus, as the cap is screwed off the runner body due to rotation of the retainer ears, the plastic clamp flaps open so that the coronary stent delivery system is in a free state enabling its free axial displacement and, once the cap is screwed on, the clamp flaps close to fix the delivery system.

When the device is prepared for use, a coronary stent carried by a delivery system is first progressively inserted inside the device while the clamp flaps are open, and the coronary stent delivery system is placed via through-holes provided in the housing. The operator manually advances the coronary stent carried by the delivery system placed within the device to the affected area of a coronary artery. Then, the operator brings the device to a necessary distance for fixing the same with his/her left arm, fixes the delivery system with the aid of clamp flaps by means of rotating the retainer with his/her right hand and further rotates the cylindrical rear part of the housing to convert rotary motion of the housing into translational motion of the runner, and advances the delivery system to a necessary distance for positioning the coronary stent inside the vessel. When advancing the rear part of the housing the operator may also return the mechanism retaining the coronary stent delivery system into its initial position coronary stent delivery system by means of rotating the cylindrical rear part of the housing in the necessary direction, so that further positioning of the coronary stent either forwards or backwards may be continued.

Exemplary Embodiment 3

The device comprises a housing having a runner disposed therein, said runner having a hole for receiving a delivery system, projections for engaging an internal thread of the cylindrical rear part of the housing and projections for moving along guides inside the housing on the one side, and a plastic clamp provided with a hole for receiving a delivery system, rotatable around its axis, placed in a cap with a hole for receiving the delivery system and provided with a thread to be screwed on the runner on the other side.

The housing formed of a truncated cylindrical front part and a cylindrical rear part connected to each other by a circumferentially extending slot is made of plastic and is provided with recesses for operator's finger on both sides of the truncated cylindrical front part of the housing, wherein the right and left halves of the body are manufactured separately, and connected to each other once the mechanism has been assembled with the aid of projections and holes arranged on the edges of the inner part of the housing.

The cylindrical front part of the housing is provided with a retainer having ears projecting into the side holes on both sides of the housing inside which a cap is arranged threadedly connected to the runner accommodating a plastic clamp.

In the truncated front part of the housing adapted for being held with the operator's left thumb and left forefinger, recesses are formed allowing the operator to fix the device in position, wherein the left thumb recess also serves as a pad for fixing a coronary guide. Through-holes for insertion of the coronary stent delivery system into the housing are formed in the front and rear parts of the housing.

A slot is formed circumferentially in the housing between its truncated part and cylindrical part, connecting both parts such that the cylindrical rear part is rotatable around its axis.

Accommodated in side cutouts on the front part of the housing are the ears of the retainer arranged inside the housing, said ears allowing the retainer to be rotatable relative to the housing in the slots of which projections are arranged on the runner cup accommodating a plastic clamp rotatable around its axis, said clamp, once engaged, causing the cap to rotate in one or another direction as the cap either screws on or off the runner and thereby compressing or expanding the plastic clamp flaps respectively clamping or releasing the coronary stent delivery system. At the same time, the cap moves horizontally along the same slots together with the runner as the cylindrical rear part of the housing rotates at the point of the connection slot.

The retainer is formed such that as it is caused to rotate with the aid of ears provided in the side cutouts in the cylindrical front part of the housing, the cap rotates to become screwed on or off with the clamp inside, wherein the clamp flaps open and close depending on the cap position, and as the cylindrical rear part of the housing rotates around its axis, the runner moves horizontally along the guides of the front part of the housing once its projections have engaged the internal thread in the cylindrical rear part of the housing. The coronary stent delivery system arranged in the runner moves simultaneously with the runner while the clamp flaps are clamped.

In order to return the retention mechanism to its initial position, the retainer and the cylindrical rear part of the housing are caused to operate in reverse direction.

Such design makes it possible to rigidly fix coronary stent delivery system as the stent moves both forwards and backwards while allowing the same to rotate simultaneously around its axis.

Thus, as the cap is screwed off the runner body due to rotation of the retainer ears the plastic clamp flaps open and coronary stent delivery system is in a free state enabling its free axial displacement and, once the cap is screwed on, the clamp flaps close to fix the delivery system.

When the device is prepared for use, a coronary stent carried by a delivery system is first progressively inserted inside the device while the clamp flaps are open and the coronary stent delivery system is placed via through-holes provided in the housing. The operator manually advances the coronary stent carried by the delivery system placed within the device to an affected area of a coronary artery. Then, the operator brings the device to a necessary distance for fixing the same with his/her left arm, fixes the delivery system with the aid of clamp flaps by means of rotating the retainer with his/her right hand and further rotates the cylindrical rear part of the housing to convert rotary motion of the housing into translational motion of the runner and advances the delivery system to a necessary distance for positioning the coronary stent inside the vessel. When advancing the rear part of the housing the operator may also return the mechanism retaining the coronary stent delivery system into its initial position coronary stent delivery system by means of rotating the cylindrical rear part of the housing in the necessary direction so that further positioning of the coronary stent either forwards or backwards may be continued.

Exemplary Embodiment 4

The device comprises a housing having a runner disposed therein, said runner having a hole for receiving a delivery system, projections for engaging an internal thread of a cylindrical rear part of the housing, projections for moving along guides inside the housing on the one side and a cap provided with a hole for receiving the delivery system and a rubber bush provided with a hole for receiving the delivery system inside therein and with cone-shaped end surfaces matching similar surfaces inside the cap and the runner, said bush placed in the cap and provided with a thread to be screwed on the runner on the other side.

The housing formed of a truncated cylindrical front part and cylindrical rear part connected to each other by a circumferentially extending slot is made of plastic and is provided with recesses for operator's fingers on both sides of the front part of the housing, wherein the right and left halves of the body are manufactured separately and connected to each other once the mechanism has been assembled with the aid of projections and holes arranged on the edges of the inner part of the housing.

The cylindrical front part of the housing is provided with a retainer having ears projecting into the side holes on both sides of the housing inside which a cap is arranged threadedly connected to the runner accommodating a rubber bush.

In the truncated front part of the housing adapted for being held with the operator's left thumb and left forefinger, recesses are formed allowing the operator to fix the device in position, wherein the left thumb recess also serves as a pad for fixing a coronary guide. Through-holes for insertion of the coronary stent delivery system into the housing are formed in the front and rear parts of the housing.

A circumferential slot is formed in the housing between its cylindrical front part and cylindrical rear part, connecting both parts such that the cylindrical rear part is rotatable around its axis.

Accommodated in side cutouts on the front part of the housing are the ears of the retainer arranged inside the housing, said ears allowing the retainer to be rotatable relative to the housing in the slots of which projections are arranged on the runner cup accommodating a rubber bush therein with cone-shaped end surfaces matching similar surfaces of the cap and the runner, said surfaces, once engaged, causing the cap to rotate in one or another direction as the cap either screws on or off the runner and thereby either compressing or expanding the rubber bush and respectively clamping or releasing the coronary stent delivery system. At the same time, the cap moves horizontally along the same slots together with the runner as the cylindrical rear part of the housing rotates at the point of the connection slot.

The retainer is formed such that as it is caused to rotate with the aid of ears provided in the side cutouts in the front part of the housing, the cap rotates to become screwed on or off with the rubber hush inside therein that compresses or expands depending on the cap position and as the cylindrical rear part of the housing rotates around its axis, the runner moves horizontally along the guides of the front part of the housing once its projections have engaged the internal thread in the cylindrical rear part of the housing. The coronary stent delivery system arranged in the runner moves simultaneously with the runner while the rubber bush is clamped.

In order to return the retention mechanism to its initial position, the retainer and the cylindrical rear part of the housing are caused to operate in reverse direction.

Such design makes it possible to rigidly fix coronary stent delivery system as the stent moves both forwards and backwards.

Thus, as the cap is screwed off the runner body due to rotation of the retainer ears, the rubber bush expands so that the coronary stent delivery system is in a free state enabling its free axial displacement and, once the cap is screwed on, the rubber bush compresses to fix the delivery system.

When the device is prepared for use, a coronary stent carried by a delivery system is first progressively inserted inside the device while the rubber bush is expanded and the coronary stent delivery system is placed via through-holes provided in the housing. The operator manually advances the coronary stent carried by the delivery system placed within the device to an affected area of a coronary artery. Then, the operator brings the device to a necessary distance for fixing the same with his/her left arm, fixes the delivery system with the aid of the rubber bush by means of rotating the retainer with his/her right hand and further rotates the cylindrical rear part of the housing to convert rotary motion of the housing into translational motion of the runner, and advances the delivery system to a necessary distance for positioning the coronary stent inside the vessel. When advancing the rear part of the housing the operator may also return the mechanism retaining the coronary stent delivery system into its initial position coronary stent delivery system by means of rotating the cylindrical rear part of the housing in the necessary direction so that further positioning of the coronary stent either forwards or backwards may be continued.

Provided below is a list of the attached drawings.

FIG. 1 is a general view of the device showing:
1—device housing;
2—truncated front part of the housing;
3—recess for operator's fingers;
4—hole for receiving the delivery system;
5—cylindrical front part of the housing;
10—cylindrical rear part of the housing;
23—retainer;
24—retainer ears;
31—coronary stent delivery system;
32—marks for locating the runner on the cylindrical front part of the housing;
33—marks for locating the runner on the cylindrical rear part of the housing.

Figure 2:
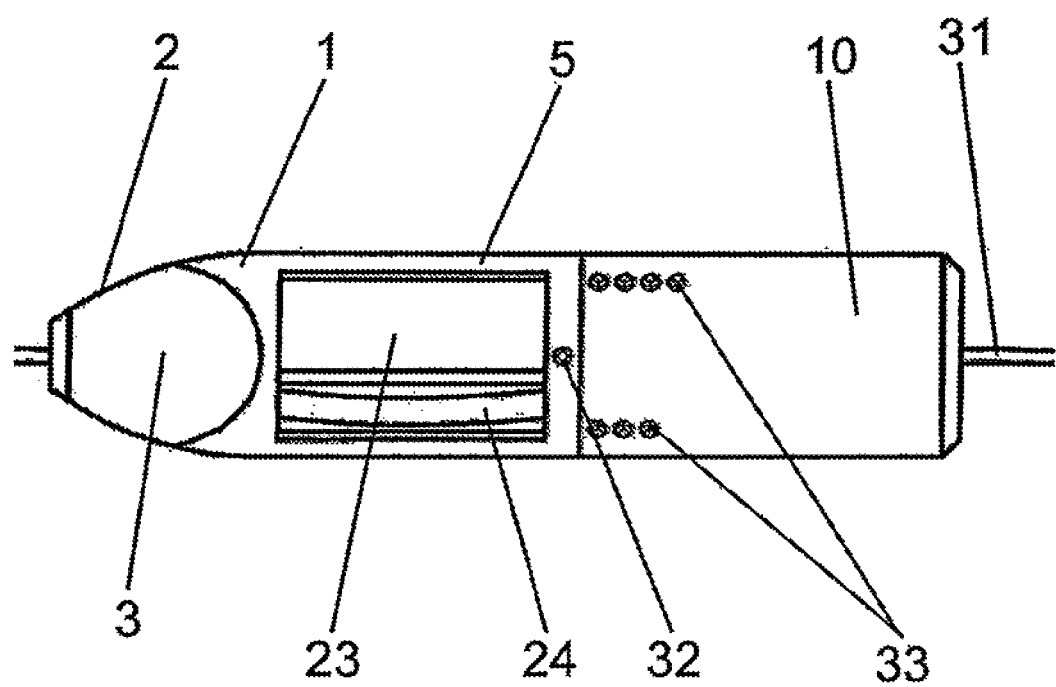

FIG. 2 is a side view showing:
1—device housing;
2—truncated front part of the housing;
3—recess for operator's fingers;
5—cylindrical front part of the housing;
10—cylindrical rear part of the housing,
23—retainer;
24—retainer ears;
31—coronary stent delivery system;
32—marks for locating the runner on the cylindrical front part of the housing;
33—marks for locating the runner on the cylindrical rear part of the housing.

Figure 3:
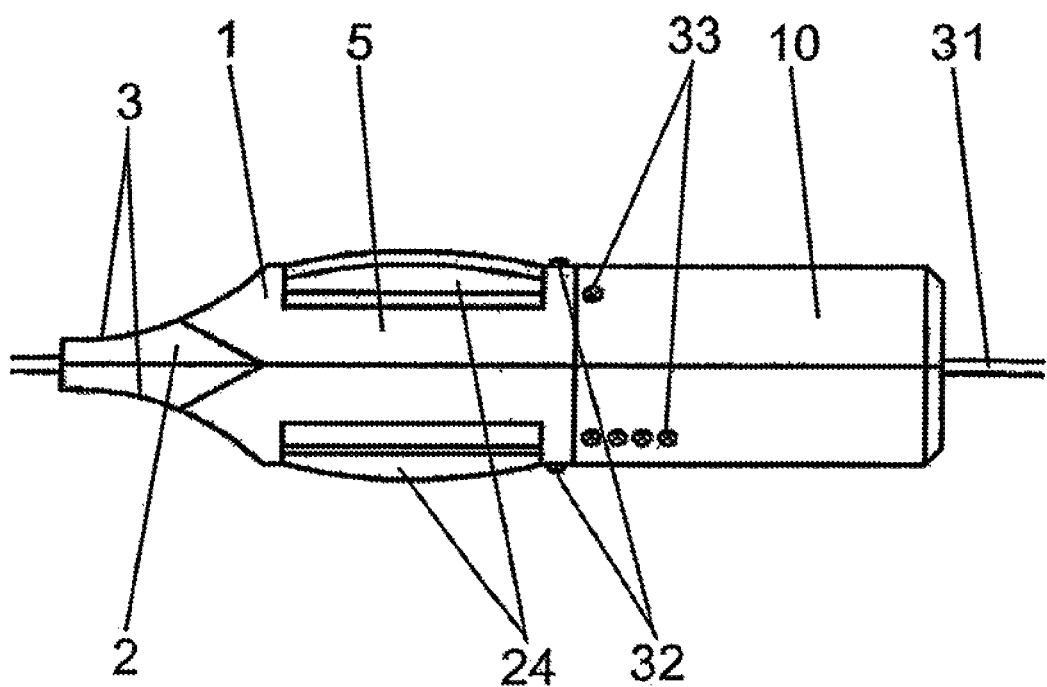

FIG. 3 is a top view showing:
1—device housing;
2—truncated front part of the housing;
3—recess for operator's fingers;
5—cylindrical front part of the housing;
10—cylindrical rear part of the housing;
24—retainer ears;
31—coronary stent delivery system;
32—marks for locating the runner on the cylindrical front part of the housing;
33—marks for locating the runner on the cylindrical rear part of the housing.

Figure 4:
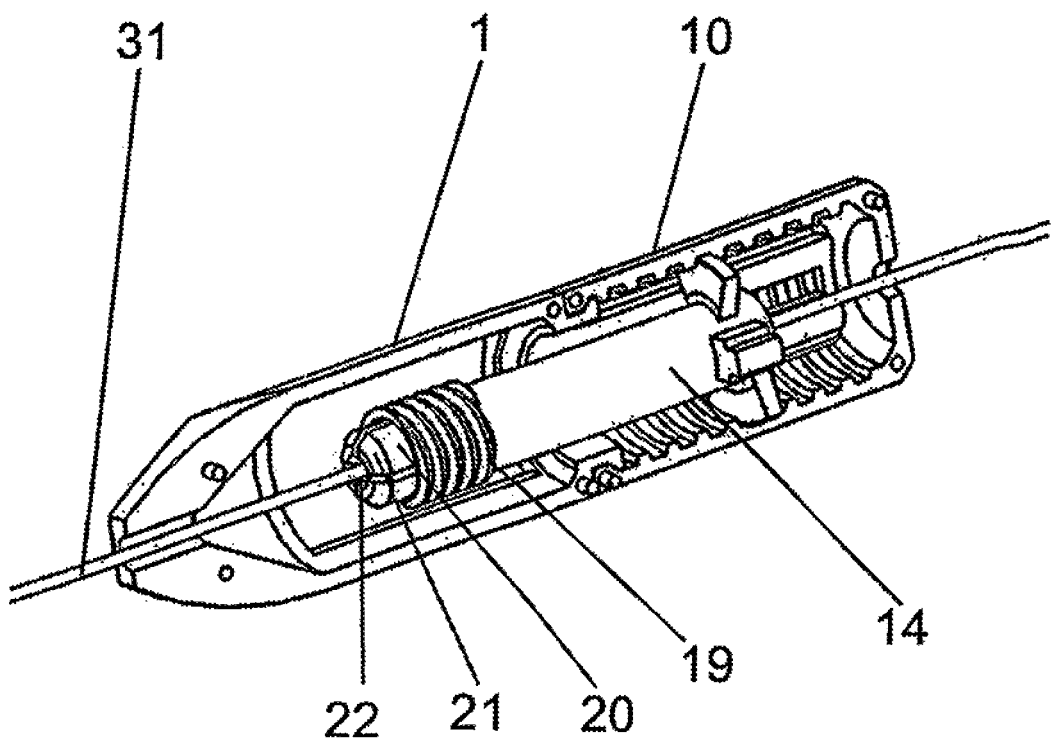

FIG. 4 is a general cross-sectional view of the device with collet hooks, showing:
1—device housing;
10—cylindrical rear part of the housing;
14—runner;
19—runner thread for screwing the cap on;
20—collet;
21—collet hooks;
22—collet hole for receiving the coronary stent delivery system;
31—coronary stent delivery system.

Figure 5:
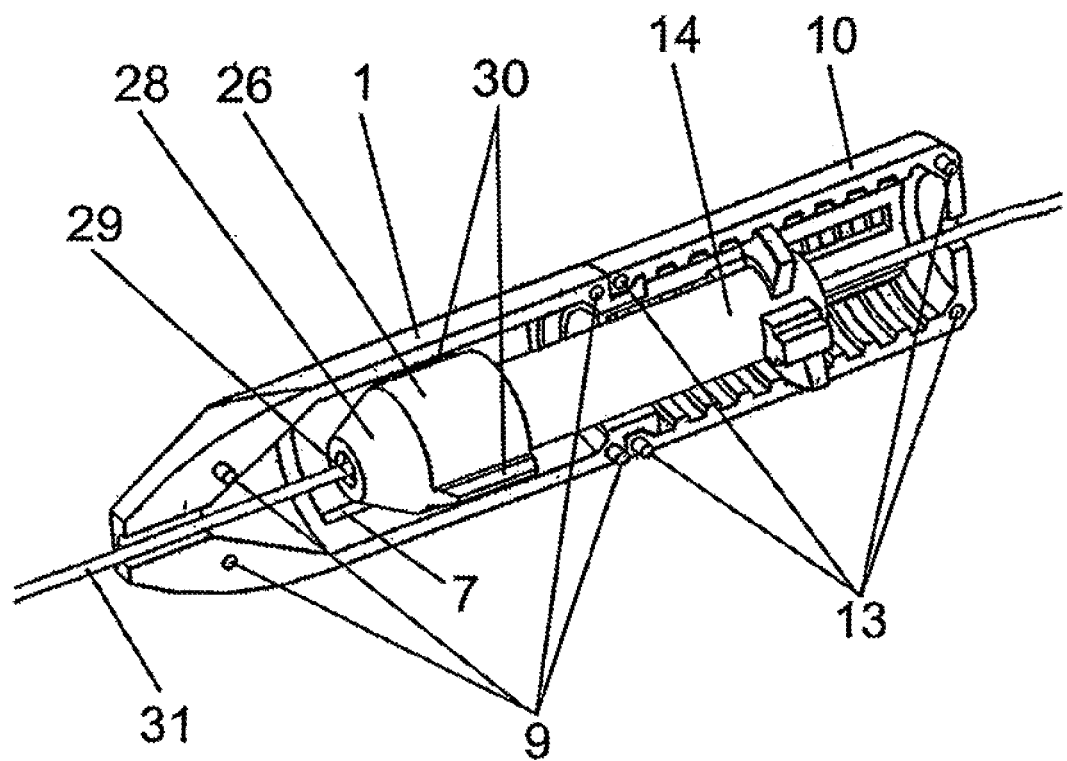

FIG. 5 is a general cross-sectional view of the device with a runner cap, showing:
1—device housing;
7—retainer cutout in the housing;
9—recesses and projections for fastening the front part of the housing;
10—cylindrical rear part of the housing;
13—recesses and projections for fastening the rear part of the housing;
14—runner;
26—cap;
28—cap cone;
29—cap hole for receiving the coronary stent delivery system,
30—cap projections;
31—coronary stent delivery system.

Figure 6:
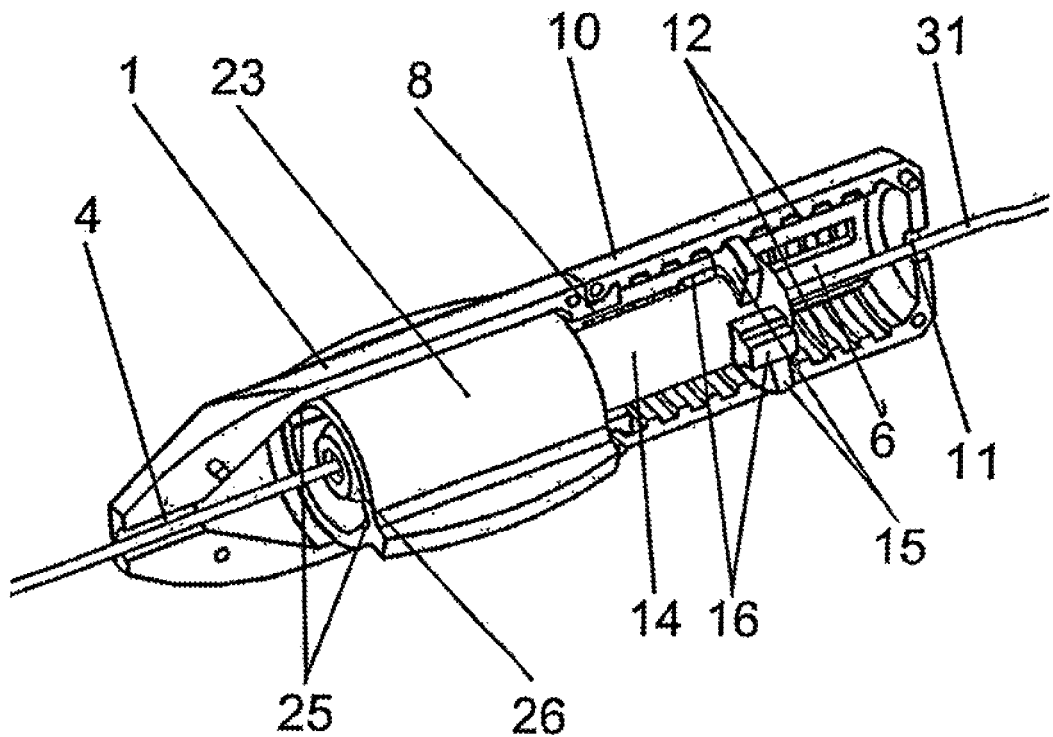
Figure 7:
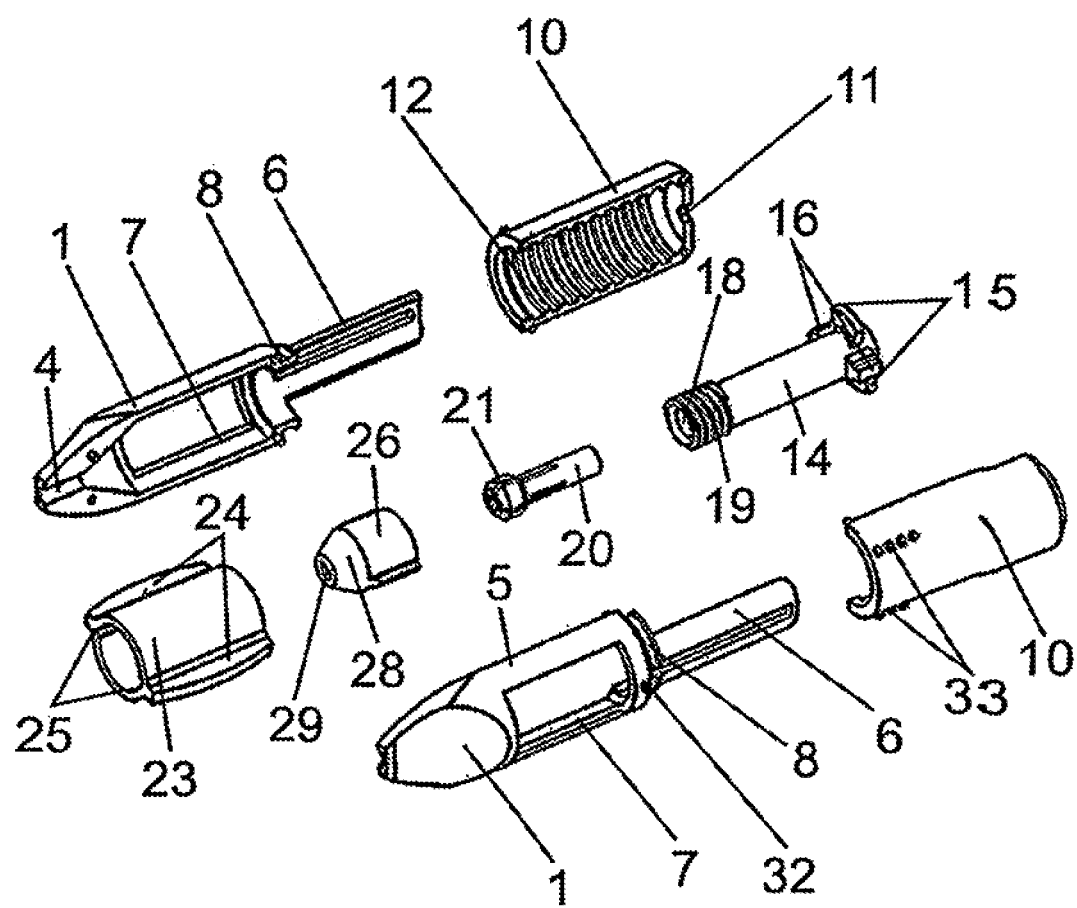
Figure 8:
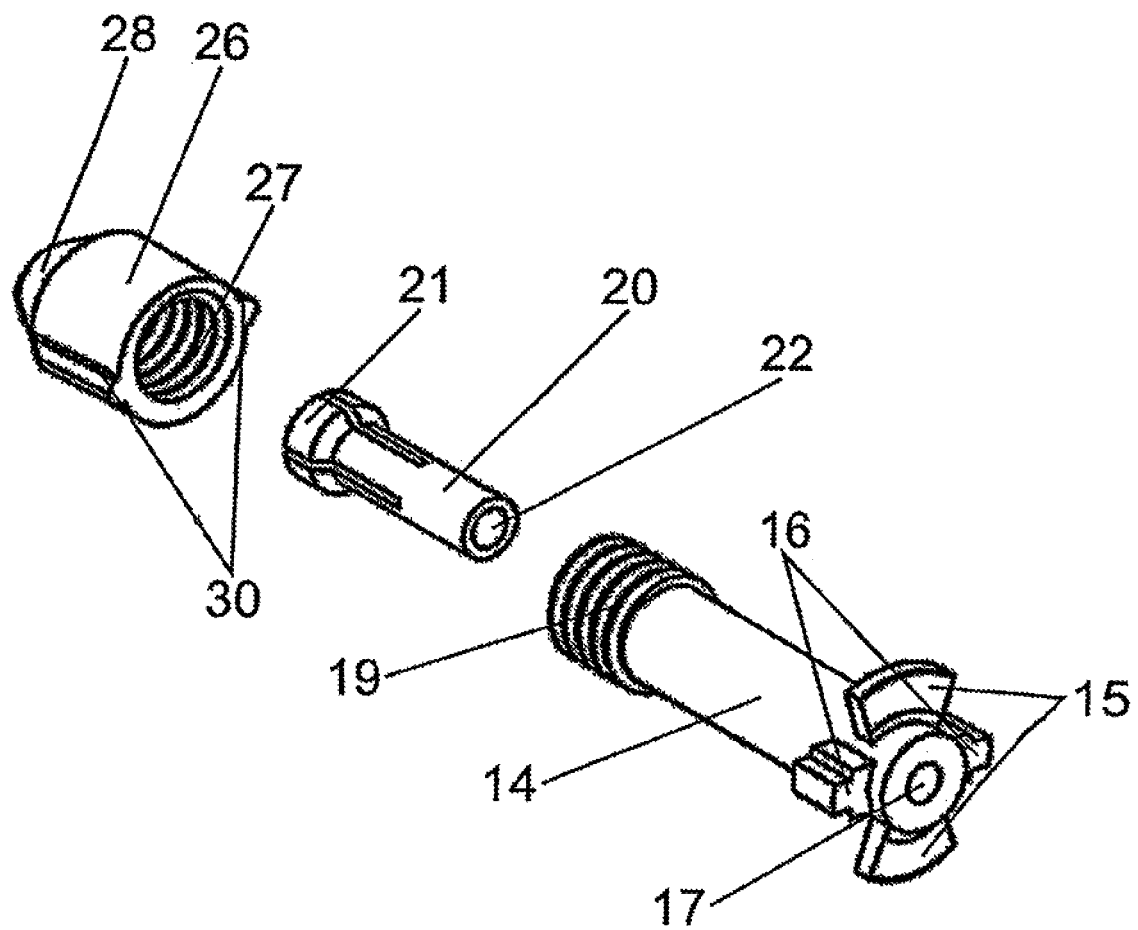
Figure 9:
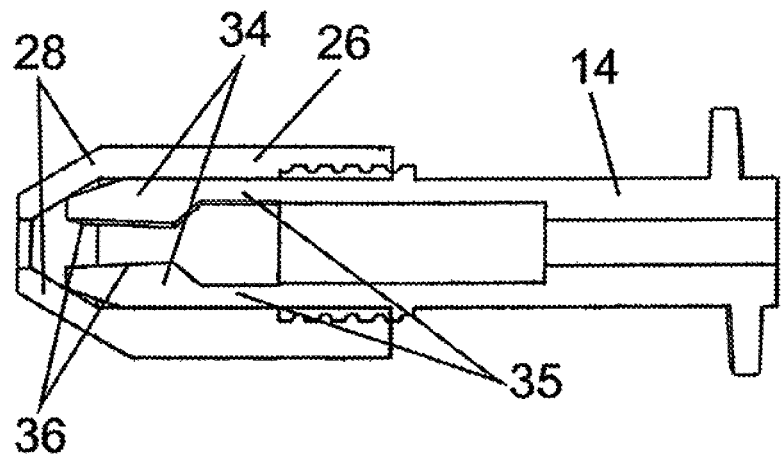
Figure 9A:
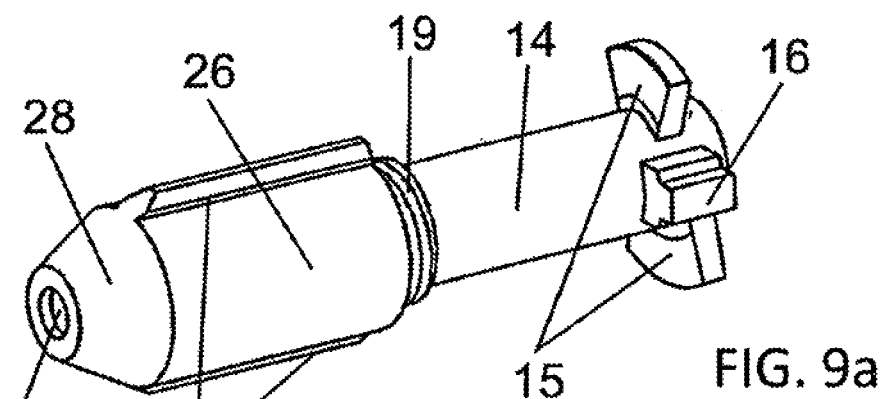
Figure 9B:
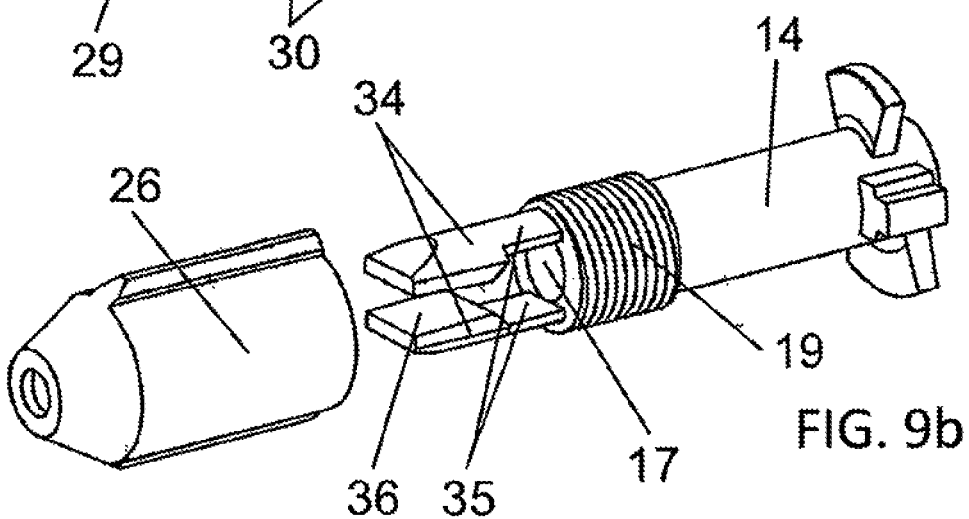
Figure 10:
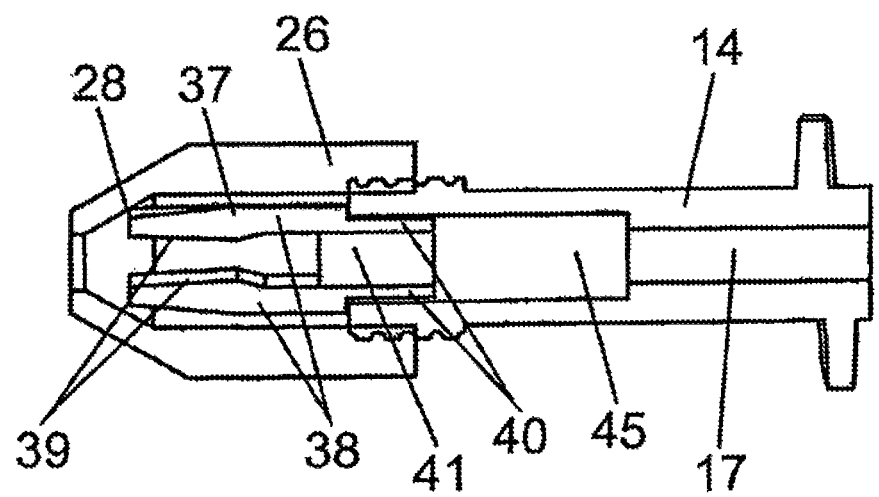
Figure 10A:
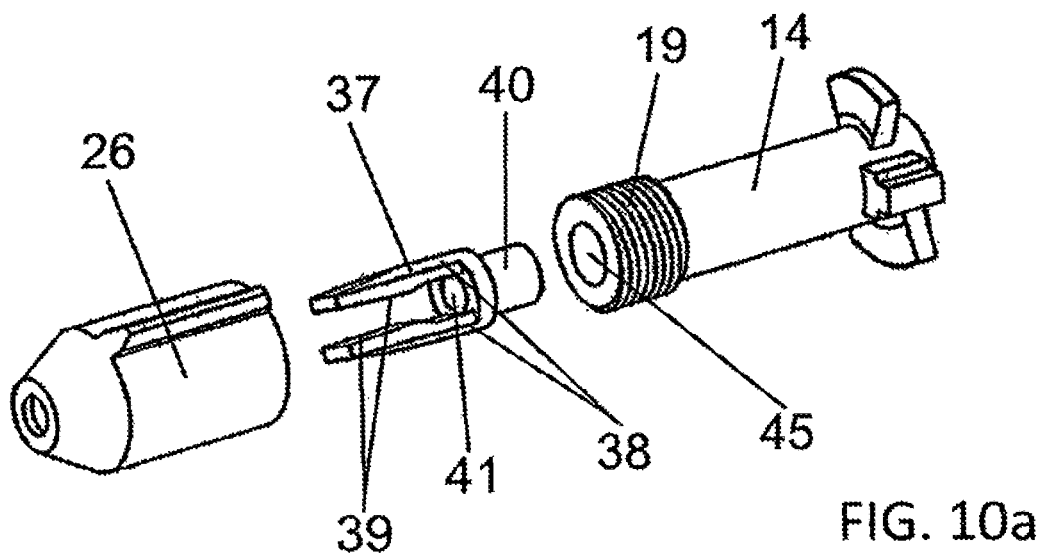
Figure 11:
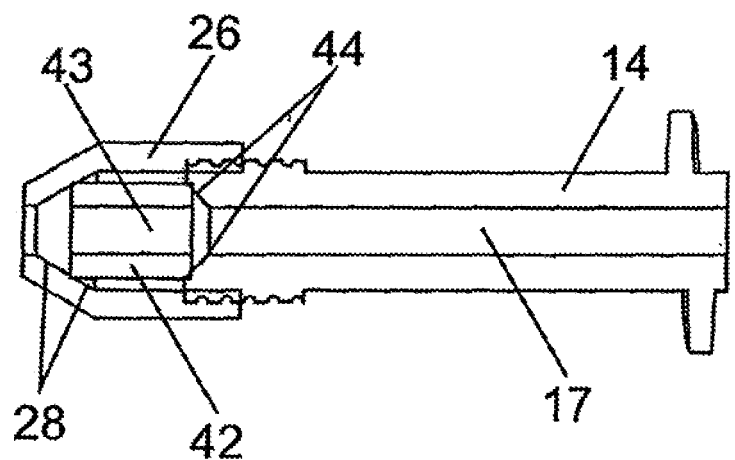
Figure 11A:
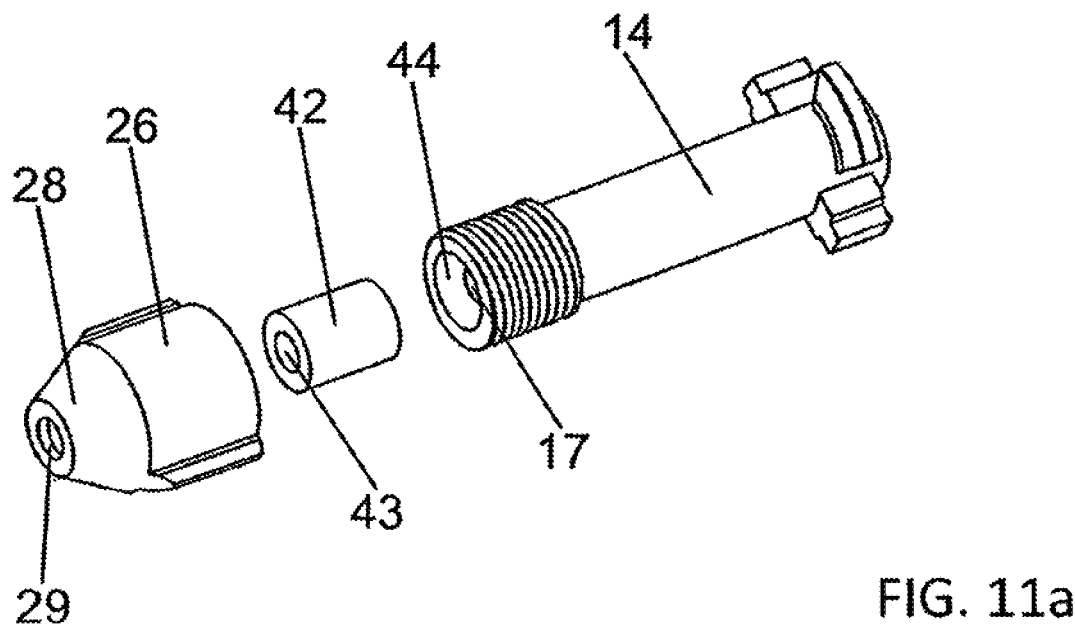

FIG. 6 is a general cross-sectional view of the device with a retainer, showing:
1—device housing;
4—hole for receiving the coronary stent delivery system;

6—runner guides;
8—slot for connecting the front and rear parts of the housing;
10—cylindrical rear part of the housing;
11—hole in the rear part of the housing for receiving the coronary stent delivery system;
12—internal thread in the rear part of the housing;
14—runner;
15—runner projections for engaging the thread inside the rear part of the housing;
16—runner projections for the housing guides;
23—retainer;
25—retainer slots;
26—cap;
31—coronary stent delivery system.
FIG. 7 is a detached view of the device, showing;
1—device housing;
4—hole for receiving the coronary stent delivery system;
6—runner guide;
7—retainer cutout in the housing;
8—slot for connecting the front and rear parts of the housing;
10—cylindrical rear part of the housing;
11—hole in the rear part of the housing for accommodating the delivery system;
12—internal thread in the rear part of the housing;
14—runner;
15—runner projections for engaging the thread inside the rear part of the housing;
16—runner projections for the housing guides;
18—runner hole for receiving the collet;
19—runner thread for screwing the cap on;
20—collet;
21—collet hooks;
23—retainer;
24—retainer ears;
25—retainer slots;
26—runner cap;
28—cap cone;
29—cap holes for accommodating the delivery system;
32—marks on the marks on the cylindrical front part of the housing;
33—marks on the rear part of the housing.
FIG. 8 is detached view of a runner, showing:
14—miner;
15—runner projections for engaging the thread inside the rear part of the housing;
16—runner projections for the housing guides;
17—runner hole for receiving the coronary stent delivery system;
19—runner thread for screwing the cap on;
20—collet;
21—collet hooks;
22—collet hole for receiving the coronary stent delivery system;
26—runner cap;
27—runner internal thread;
28—cap cone;
30—cap projections.
FIG. 9 is a general view of a runner with a sectional view of a stationary plastic clamp, showing:
14—runner;
26—cap;
28—cap cone;
34—clamp flaps;
35—clamp;
36—plastic clamp delivery system retention zone.
FIG. 9a is a general view of a runner with a stationary plastic clamp, showing:
14—runner:
15—runner projections for engaging the thread inside the rear part of the housing;
16—runner projections for the housing rear part guides;
19—runner thread for screwing the cap on;
26—runner cap;
28—cap cone;
29—cap holes for accommodating the delivery system;
30—cap projections.
FIG. 9b is a detached view of a runner with a stationary plastic clamp, showing;
14—runner;
17—runner hole for receiving the coronary stent delivery system;
19—runner thread for screwing the cap on;
26—cap;
34—clamp flaps;
35—clamp;
36—plastic clamp delivery system retention zone.
FIG. 10 is a general view of a runner with a sectional view of a movable plastic clamp, showing:
14—runner;
17—runner hole for receiving the coronary stent delivery system;
26—cap;
28—cap cone;
37—clamp flaps;
38—clamp;
39—coronary stent delivery system retention zone;
40—plastic clamp bush for connection to the runner;
41—plastic clamp hole for receiving the coronary stent delivery system;
45—runner hole for receiving the clamp bush.
FIG. 10a is a general detached view of a runner with a movable plastic clamp, showing;
14—runner;
17—runner hole for receiving the coronary stent delivery system;
19—runner thread for screwing the cap on;
26—cap;
37—clamp flaps;
38—clamp;
39—coronary stent delivery system retention zone;
40—plastic clamp bush for connection to the runner;
41—plastic clamp hole for receiving the coronary stent delivery system;
45—runner hole for receiving the clamp bush clamp bush.
FIG. 11 is a general view of a runner with a sectional view of a rubber hush, showing:
14—runner;
17—runner hole for receiving the coronary stent delivery system;
26—cap;
28—cap cone;
42—rubber bush;
43—rubber bush hole for receiving the coronary stent delivery system;
44—cone-shaped part inside the runner.
FIG. 11a is a detached view of a runner with a rubber bush, showing:
14—runner;
17—runner hole for receiving the coronary stent delivery system;
26—cap;
28—cap cone;

29—cap holes for receiving the coronary stent delivery system;
42—rubber bush;
43—rubber bush hole for receiving the coronary stent delivery system;
44—cone-shaped part inside the runner.

The present invention is further described below with reference to the attached drawings.

Exemplary Embodiment 1

The device comprises a housing 1 (FIG. 1) formed of a truncated front part 2 and a cylindrical from part 5 (FIG. 1, FIG. 2, FIG. 3) with a recess 3 for operator's fingers (FIG. 1, FIG. 2, FIG. 3), with a hole 4 for receiving the coronary stent delivery system 31 (FIG. 1, FIG. 2, FIG. 3, FIG. 4, FIG. 5, FIG. 6), and of a cylindrical rotatable rear part 10 with a hole 11 for receiving the coronary stent delivery system 31 (FIG. 1, FIG. 2, FIG. 3, FIG. 4, FIG. 5, FIG. 6) and with marks 32 on the cylindrical front part 5 extending around a slot 8 (FIG. 7) connecting the front and the rear parts of the housing, and with marks 33 on the cylindrical rotatable rear part 10 of the housing 1 (FIG. 1, FIG. 2, FIG. 3) for providing the operator with visual information as to the rotation angle of the cylindrical rear part 10 of the housing 1 (FIG. 1, FIG. 2, FIG. 3) for longitudinal displacement of a runner 14, wherein the housing 1 is made of plastic and its left and right halves (FIG. 1) are manufactured separately and connected with the aid of recesses and projections 9 and 13 in the front part of the housing and in the rear part of the housing (FIG. 5) after placing therein the runner 14 (FIG. 4, FIG. 5, FIG. 6) with a hole 17 (FIG. 8) for receiving the coronary stent delivery system 31 (FIG. 4, FIG. 5, FIG. 6) with projections 15 for engaging the thread 12 (FIG. 6, FIG. 7) in the cylindrical rear part of the housing 10 (FIG. 6, FIG. 7, FIG. 8), with projections 16 for connecting to the guides 6 in the front part of the housing (FIG. 6, FIG. 7, FIG. 8) for displacing the runner 14, with a collet 20 (FIG. 4, FIG. 7, FIG. 8) disposed in the hole 18 of the runner 14 (FIG. 7) so as to be rotatable around its axis, provided with hooks 21 (FIG. 4, FIG. 7, FIG. 8) accommodated in the runner 14 cap 26 (FIG. 5, FIG. 6, FIG. 7, FIG. 8) with a hole 29 (FIG. 5, FIG. 7) for receiving the coronary stent delivery system 31, able to screw on and off the runner 14 thread 19 (FIG. 4, FIG. 7, FIG. 8) inside the retainer 23 (FIG. 1, FIG. 2, FIG. 6, FIG. 7) and arranged in the front part 2 of the housing 1 in a cutout 7 (FIG. 1, FIG. 2, FIG. 3) with ears 24 (FIG. 1, FIG. 2, FIG. 3, FIG. 7) for rotating the retainer 23 (FIG. 1, FIG. 2, FIG. 6) and screwing the cap 26 on and off (FIG. 5, FIG. 6, FIG. 7, FIG. 8) due to engagement of the cap 26 projections 30 with slots 25 (FIG. 6, FIG. 7) as the retainer 23 rotates (FIG. 1, FIG. 2, FIG. 6).

For accommodating the delivery system 31 (FIG. 1, FIG. 2, FIG. 3) inside the device, the operator rotates the retainer 23 ears 24 (FIG. 1, FIG. 2, FIG. 3, FIG. 7) as a result of which the retainer 23 (FIG. 1, FIG. 2, FIG. 3, FIG. 7) rotates, the cap 26 projections 30 (FIG. 5, FIG. 8) become engaged with the retainer 23 slots 25 (FIG. 6. FIG. 7), the cap 26 screws off the runner 14 thread 19 (FIG. 4), the collet 20 hooks 21 open (FIG. 4) to release the hole 22 (FIG. 4, FIG. 8) for receiving the coronary stent delivery system 31 in the device 1. The delivery system 31 (FIG. 1, FIG. 2, FIG. 4, FIG. 5, FIG. 6) is inserted through the opening 11 in the cylindrical rear part of the housing 10 (FIG. 6, FIG. 7), opening 17 in the runner 14 (FIG. 8), opening 29 in the cap 26 (FIG. 5, FIG. 7) and opening 4 in the front part 2 of the housing (FIG. 6, FIG. 7).

Then, the retainer 23 is caused to rotate in an opposite direction (FIG. 5) with the aid of the retainer 23 ears 24 (FIG. 1, FIG. 2, FIG. 3, FIG. 7) as a result of which the runner 14 cap 26 screws on the runner 14 thread 19 (FIG. 5) to close the collet 20 hooks 21 and to fix the delivery system. By means of rotating the cylindrical rear part 10 of the housing 1, the operator converts rotary motion of the rear part 10 of the housing 1 (FIG. 1, FIG. 2, FIG. 3) into translational motion of the runner 14 (FIG. 4, FIG. 5, FIG. 6) and advances the delivery system 31 horizontally inside the device so that it is rotatable around its axis while further controlling visually the advancement with the aid of special marks 32 and 33 on the front part 5 and on the cylindrical rear part 10 of the housing 1 (FIG. 1, FIG. 2, FIG. 3), respectively.

Exemplary Embodiment 2

The device comprises a housing 1 (FIG. 1) formed of a truncated front part 2 and a cylindrical part 5 (FIG. 1, FIG. 2, FIG. 3) with a recess 3 for operator's fingers (FIG. 1, FIG. 2, FIG. 3), with a hole 4 for receiving the coronary stent delivery system 31 (FIG. 1, FIG. 2, FIG. 3, FIG. 4, FIG. 5, FIG. 6) and of a cylindrical rotatable rear part 10 with a hole 11 for receiving the coronary stent delivery system 31 (FIG. 1, FIG. 2, FIG. 3, FIG. 4, FIG. 5, FIG. 6) and with marks 32 on the cylindrical front part 5 of the housing 1 extending around a slot 8 (FIG. 7) connecting the front and the rear parts of the housing, and with marks 33 on the cylindrical rotatable rear part 10 of the housing 1 (FIG. 1, FIG. 2, FIG. 3) for providing the operator with visual information as to the rotation angle of the cylindrical rear part 10 of the housing 1 (FIG. 1, FIG. 2, FIG. 3) for longitudinal displacement of a runner 14, wherein the housing 1 is made of plastic and its left and right halves (FIG. 1) are manufactured separately and connected with the aid of recesses and projections 9 and 13 in the front part of the housing and in the rear part of the housing (FIG. 5) after placing therein the runner 14 (FIG. 4, FIG. 5, FIG. 6) with a hole 17 (FIG. 8) for receiving the coronary stent delivery system 31 (FIG. 4, FIG. 5, FIG. 6), with projections 15 for engaging the thread 12 (FIG. 6, FIG. 7) cylindrical rear part of the housing 10 (FIG. 6, FIG. 7, FIG. 8), projections 16 for connecting to the guides 6 in the front part of the housing (FIG. 6, FIG. 7, FIG. 8) for displacing the runner 14 with a clamp 35 (FIG. 9*a*, FIG. 9*b*) formed integrally with the runner 14 (FIG. 9*a*) provided with flaps 34 (FIG. 9*a*, FIG. 9*b*) having a clamp delivery system retention zone 36 and accommodated in the runner 14 cap 26 (FIG. 9, FIG. 9*a*, FIG. 9*b*) with a hole 29 (FIG. 9) for receiving the coronary stent delivery system 31, able to screw on and off the runner 14 thread 19 (FIG. 9, FIG. 9*b*) inside the retainer 23 (FIG. 1, FIG. 2, FIG. 6, FIG. 7), arranged in the front part 2 of the housing 1 in a cutout 7 (FIG. 1, FIG. 2, FIG. 3) with ears 24 (FIG. 1, FIG. 2, FIG. 3, FIG. 7) for rotating the retainer 23 (FIG. 1, FIG. 2, FIG. 6) and screwing the cap 26 on and off (FIG. 5, FIG. 6, FIG. 7, FIG. 8, FIG. 9, FIG. 9*a*, FIG. 9*b*) due to engagement of the cap 26 projections 30 with slots 25 (FIG. 6, FIG. 7) as the retainer 23 rotates (FIG. 1, FIG. 2, FIG. 6).

For accommodating the delivery system 31 (FIG. 1, FIG. 2, FIG. 3) inside the device, the operator rotates the retainer 23 ears 24 (FIG. 1, FIG. 2, FIG. 3, FIG. 7) as a result of which the retainer 23 (FIG. 1, FIG. 2, FIG. 3, FIG. 7) rotates, the cap 26 projections 30 (FIG. 5, FIG. 9*a*) become engaged with the retainer 23 slots 25 (FIG. 6, FIG. 7), the cap 26 screws off the runner 14 thread 19 (FIG. 9*a*, 9*b*), the clamp 35 flaps 34 open (FIG. 9, 9*b*) to release the hole 17 (FIG. 9*b*)

for receiving the coronary stent delivery system 31 in the device. The delivery system 31 (FIG. 1, FIG. 2, FIG. 4, FIG. 5, FIG. 6) is inserted through the opening 11 in the cylindrical rear part of the housing 10 (FIG. 6, FIG. 7), opening 17 in the runner 14 (FIG. 8, FIG. 9*b*), opening 29 in the cap 26 (FIG. 5, FIG. 9*a*) and opening 4 in the front part 2 of the housing (FIG. 6, FIG. 7).

Then, the retainer 23 is caused to rotate in an opposite direction (FIG. 5) with the aid of the retainer 23 ears 24 (FIG. 1, FIG. 2, FIG. 3, FIG. 7) as a result of which the runner 14 cap 26 FIG. 9, FIG. 9*a*, FIG. 9*b*) screws on the runner 14 thread 19 (FIG. 5, FIG. 9*a*, FIG. 9*b*) to close the flaps 34 in the clamp delivery system retention zone 36 (FIG. 9, FIG. 9*b*) of the clamp 35 formed integrally with the runner 14 to fix the delivery system.

By means of rotating the cylindrical rear part 10 of the housing 1, the operator converts rotary motion of the rear part 10 of the housing 1 (FIG. 1, FIG. 2, FIG. 3) into translational motion of the runner 14 (FIG. 4, FIG. 5, FIG. 6, FIG. 9, FIG. 9*a*, FIG. 9*b*) and advances the delivery system 31 horizontally inside the device while further controlling visually the advancement with the aid of special marks 32 and 33 on the front part 5 and cylindrical rear part 10 of the housing 1 (FIG. 1, FIG. 2, FIG. 3).

Exemplary Embodiment 3

The device comprises a housing 1 (FIG. 1), formed of a truncated front part 2 and a cylindrical part 5 of the housing 1 (FIG. 1, FIG. 2, FIG. 3) with a recess 3 for operator's fingers (FIG. 1, FIG. 2, FIG. 3), with a hole 4 for receiving the coronary stent delivery system 31 (FIG. 1, FIG. 2, FIG. 3, FIG. 4, FIG. 5, FIG. 6), и cylindrical rotatable rear part 10 of the housing 1 with a hole 11 for receiving the coronary stent delivery system 31 (FIG. 1, FIG. 2, FIG. 3, FIG. 4, FIG. 5, FIG. 6) and with marks 32 on the cylindrical front part 5 of the housing 1 extending around a slot 8 (FIG. 7) connecting the front and the rear parts of the housing, and with marks 33 on the cylindrical rotatable rear part 10 of the housing 1 (FIG. 1, FIG. 2, FIG. 3) for providing the operator with visual information as to the rotation angle of the cylindrical rear part 10 of the housing 1 (FIG. 1, FIG. 2, FIG. 3) for longitudinal displacement of a runner 14, wherein the housing 1 is made of plastic and its left and right halves (FIG. 1) are manufactured separately and connected with the aid of recesses and projections 9 and 13 in the front part and rear part of the housing (FIG. 5) after placing therein the runner 14 (FIG. 4, FIG. 5, FIG. 6) with a hole 17 (FIG. 8) for receiving the coronary stent delivery system 31 (FIG. 4, FIG. 5, FIG. 6), with projections 15 for engaging the thread 12 (FIG. 6, FIG. 7) in the cylindrical rear part of the housing 10 (FIG. 6, FIG. 7, FIG. 8), with projections 16 for connecting to the guides 6 in the front part of the housing (FIG. 6, FIG. 7, FIG. 8) for displacing the runner 14, with a clamp 38 (FIG. 10, FIG. 10*a*) disposed in the runner hole 45 for receiving the clamp 40 bush (FIG. 10*a*) as to be rotatable around its axis, provided with flaps 37 having a stent delivery system retention zone 39 (FIG. 10, FIG. 10*a*), with a hole 41 (FIG. 10, FIG. 10*a*) for receiving the coronary stent delivery system 31, accommodated in the runner 14 cap 26 (FIG. 10 FIG. 10*a*), able to screw on and off the runner 14 thread 19 (FIG. 10*a*) inside the retainer 23 (FIG. 1, FIG. 2, FIG. 6, FIG. 7), and arranged in the front part 2 of the housing 1 in a cutout 7 (FIG. 1, FIG. 2, FIG. 3) with ears 24 (FIG. 1, FIG. 2, FIG. 3, FIG. 7) for rotating the retainer 23 (FIG. 1, FIG. 2, FIG. 6) and screwing the cap 26 on and off (FIG. 5, FIG. 6, FIG. 7, FIG. 8, FIG. 10, FIG. 10*a*) due to engagement of the cap 26 projections 30 with slots 25 (FIG. 6, FIG. 7) as the retainer 23 rotates (FIG. 1, FIG. 2, FIG. 6).

For accommodating the delivery system 31 (FIG. 1, FIG. 2, FIG. 3) inside the device, the operator rotates the retainer 23 ears 24 (FIG. 1, FIG. 2, FIG. 3, FIG. 7) as a result of which the retainer 23 (FIG. 1, FIG. 2, FIG. 3, FIG. 7) rotates, the cap 26 projections 30 (FIG. 5, FIG. 10*a*) become engaged with the retainer 23 slots 25 (FIG. 6, FIG. 7), the cap 26 screws off the runner 14 thread 19 (FIG. 10, FIG. 10*a*), the flaps 37 of the clamp 38 (FIG. 10*a*) accommodated in the runner 14 bush 18 (FIG. 10*a*) open to release the clamp 38 hole 41 (FIG. 10, FIG. 10*a*) for receiving the coronary stent delivery system 31 in the device. The delivery system 31 (FIG. 1, FIG. 2, FIG. 4, FIG. 5, FIG. 6) is inserted through the opening 11 in the cylindrical rear part of the housing 10 (FIG. 6, FIG. 7), opening 17 in the runner 14 (FIG. 10), opening 29 in the cap 26 (FIG. 5, FIG. 10*a*) and opening 4 in the front part 2 of the housing (FIG. 6, FIG. 7).

Then, the retainer 23 is caused to rotate in an opposite direction (FIG. 5) with the aid of the retainer 23 ears 24 (FIG. 1, FIG. 2, FIG. 3, FIG. 7) as a result of which the runner 14 cap 26 FIG. 10, FIG. 10*a*) screws on the runner 14 thread 19 (FIG. 5, FIG. 10*a*) to close the flaps 37 in the stent delivery system retention zone 39 of the clamp 38 (FIG. 10, FIG. 10*a*) to fix the delivery system.

By means of rotating the cylindrical rear part 10 of the housing 1, the operator converts rotary motion of the rear part 10 of the housing 1 (FIG. 1, FIG. 2, FIG. 3) into translational motion of the runner 14 (FIG. 4, FIG. 5, FIG. 6, FIG. 10, FIG. 10*a*) and advances the delivery system 31 horizontally inside the device so that it is rotatable around its axis while further controlling visually the advancement with the aid of special marks 32 and 33 on the front part 5 and cylindrical rear part 10 of the housing 1 (FIG. 1, FIG. 2, FIG. 3), respectively.

Exemplary Embodiment 4

The device comprises a housing 1 (FIG. 1), formed off truncated front part 2 and a cylindrical part 5 of the housing 1 (FIG. 1, FIG. 2, FIG. 3) with a recess 3 for operator's fingers (FIG. 1, FIG. 2, FIG. 3), with a hole 4 for receiving the coronary stent delivery system 31 (FIG. 1, FIG. 2, FIG. 3, FIG. 4, FIG. 5, FIG. 6), and a cylindrical rotatable rear part 10 of the housing 1 with a hole 11 for receiving the coronary stent delivery system 31 (FIG. 1, FIG. 2, FIG. 3, FIG. 4, FIG. 5, FIG. 6) and with marks 32 on the cylindrical front part 5 of the housing 1 extending around a slot 8 (FIG. 7), connecting the front and the rear parts of the housing, and with marks 33 on the cylindrical rotatable rear part 10 of the housing 1 (FIG. 1, FIG. 2, FIG. 3) for providing the operator with visual information as to the rotation angle of the cylindrical rear part 10 of the housing 1 (FIG. 1, FIG. 2, FIG. 3) for longitudinal displacement of a runner 14, wherein the housing 1 is made of plastic and its left and right halves (FIG. 1) are manufactured separately and connected with the aid of recesses and projections 9 and 13 in the front part and rear part of the housing 1 (FIG. 5) after placing therein the runner 14 (FIG. 4, FIG. 5, FIG. 6) with a hole 17 (FIG. 8) for receiving the coronary stent delivery system 31 (FIG. 4, FIG. 5, FIG. 6), with projections 15 for engaging the thread 12 (FIG. 6, FIG. 7) cylindrical rear part of the housing 10 (FIG. 6, FIG. 7, FIG. 8), with projections 16 for connecting to the guides 6 in the front part of the housing (FIG. 6, FIG. 7, FIG. 8) for displacing the runner 14, with a rubber bush 42 (FIG. 11, FIG. 11*a*), with cone-shaped end surfaces matching similar surfaces inside a cap and the runner, with a hole 43 for receiving the coronary stent delivery system accommodated in a cap 26 (FIG. 11, FIG. 11a), able to screw on and off the runner 14 thread 19 (FIG. 11a) inside the retainer 23 (FIG. 1, FIG. 2. FIG. 6, FIG. 7) accommodated in the front part 2 of the housing 1 in a cutout 7 (FIG. 1, FIG. 2, FIG. 3) with ears 24 (FIG. 1, FIG. 2, FIG. 3, FIG. 7) for rotating the retainer 23 (FIG. 1, FIG. 2, FIG. 6) and screwing the cap 26 on and off (FIG. 5, FIG. 6, FIG. 7, FIG. 8, FIG. 11, FIG. 11a) due to engagement of the cap 26 projections 30 with slots 25 (FIG. 6, FIG. 7) as the retainer 23 rotates (FIG. 1, FIG. 2, FIG. 6).

For accommodating the delivery system 31 (FIG. 1, FIG. 2, FIG. 3) inside the device, the operator rotates the retainer 23 ears 24 (FIG. 1, FIG. 2, FIG. 3, FIG. 7) as a result of which the retainer 23 (FIG. 1, FIG. 2, FIG. 3, FIG. 7) rotates, the cap 26 projections 30 (FIG. 5, FIG. 11, FIG. 11a) become engaged with the retainer 23 slots 25 (FIG. 6, FIG. 7), the cap 26 screws off the runner 14 thread 19 (FIG. 11a), the rubber bush 42 (FIG. 11, FIG. 11a) accommodated in a cone-shaped part 44 of the runner 14 (FIG. 11, FIG. 11a) on the one side and in the cap 26 (FIG. 11, FIG. 11a) on the other side expands and release the opening 17 (FIG. 9b) for receiving the coronary stent delivery system 31 in the device. The delivery system 31 (FIG. 1, FIG. 2, FIG. 4, FIG. 5, FIG. 6) is inserted through the opening 11 in the cylindrical rear part of the housing 10 (FIG. 6, FIG. 7), opening 17 in the runner 14 (FIG. 8, FIG. 11, FIG. 11a), opening 43 in the rubber bush 42 (FIG. 11, FIG. 11a), opening 29 in the cap 26 (FIG. 5, FIG. 11a) and opening 4 in the front part 2 of the housing (FIG. 6, FIG. 7).

Then, the retainer 23 is caused to rotate in an opposite direction (FIG. 5) with the aid of the retainer 23 ears 24 (FIG. 1, FIG. 2, FIG. 3, FIG. 7) as a result of which the runner 14 cap 26 FIG. 11, FIG. 11a) screws on the runner 14 thread 19 (FIG. 5, FIG. 11a) and compresses the rubber bush 42 (FIG. 11, FIG. 11a) to fix the delivery system.

By means of rotating the cylindrical rear part 10 of the housing 1, the operator converts rotary motion of the rear part 10 of the housing 1 (FIG. 1, FIG. 2, FIG. 3) into translational motion of the runner 14 (FIG. 4, FIG. 5, FIG. 6, FIG. 11, FIG. 11a) and advances the delivery system 31 horizontally inside the device while further controlling visually the advancement with the aid of special marks 32 and 33 on the front part 5 and cylindrical rear part 10 of the housing 1 (FIG. 1, FIG. 2, FIG. 3), respectively.

The invention claimed is:

1. A device for positioning a coronary stent within coronary arteries, comprising a housing having a cylindrical front part and an internally-threaded cylindrical rear part connected to each other by a slot allowing the cylindrical rear part to rotate around an axis, wherein the cylindrical front part of the housing is provided with recesses for fixing a coronary guide;
a runner provided with projections for engaging an internal thread of the cylindrical rear part of the housing, projections for moving along guides inside the cylindrical front part on one side, and clamping means disposed in a threaded runner cap on another side, wherein inside the runner is disposed a retainer with ears projecting into side holes on both sides of the housing, and the retainer is provided with retainer slots inside for receiving side projections of the threaded runner cap, wherein the clamping means is operable by rotation of the cylindrical rear part of the device housing and comprises:
   a) a metal collet accommodated in the runner with hooks; or
   b) a plastic clamp formed integrally with the runner; or
   c) a plastic clamp formed to be rotatable around an axis; or
   d) a rubber bush arranged within the threaded runner cap, provided with cone-shaped end surfaces matching internal cone-shaped surfaces of the threaded runner cap and the runner.

2. The device according to claim 1, wherein marks are formed on the cylindrical front part of the housing along the slot connecting the cylindrical front part to the cylindrical rear part of the housing and also on the cylindrical rear part of the housing.

3. A method for positioning a coronary stent within coronary arteries, comprising accommodating a coronary stent delivery system in a device housing;
rotating retainer ears of a retainer in a first direction so that side projections of a cap arranged inside the retainer rotate together with retainer slots to screw the cap off a runner to open clamping means and form through-holes for receiving the coronary stent delivery system;
placing the coronary stent delivery system on guides extending via the through-holes in front and rear parts of the device housing and rotating the retainer ears in an opposite direction to screw the cap on the runner and to compress the clamping means to fix the coronary stent delivery system inside the device housing wherein rotary motion of the rear part of the device housing is converted into translational motion of the runner as a result of engagement of projections on an end of the runner with an internal thread in the rear part of the device housing; wherein the fixed coronary stent delivery system is displaced horizontally inside the device housing to a distance while the clamping means is caused to rotate around an axis and a coronary guide is pressed by an operator's arm against a recess formed on a truncated front part of the housing; and
wherein the clamping means is operated by rotation of the rear part of the device housing and comprises:
   a) a metal collet accommodated in the runner with hooks; or
   b) a plastic clamp formed integrally with the runner; or
   c) a plastic clamp formed to be rotatable around an axis; or
   d) a rubber bush arranged within the cap, provided with cone-shaped end surfaces matching internal cone-shaped surfaces of the cap and the runner.

* * * * *